United States Patent
Dobkine et al.

(10) Patent No.: US 7,409,954 B2
(45) Date of Patent: Aug. 12, 2008

(54) METHOD FOR TREATMENT OF INFECTIONS WITH ULTRAVIOLET LASER LIGHT

(75) Inventors: Vadim G. Dobkine, Moscow (RU); Alexander E. Dudelzak, Nepean (CA); Guennadi P. Kouzmine, Moscow (RU); Mark A. Miller, Montreal (CA); Olga V. Lovacheva, Moscow (RU)

(73) Assignee: Genestho Inc. (CA)

( * ) Notice: Subject to any disclaimer, the term of this patent is extended or adjusted under 35 U.S.C. 154(b) by 226 days.

(21) Appl. No.: 10/491,426

(22) PCT Filed: Aug. 7, 2003

(86) PCT No.: PCT/CA03/01186

§ 371 (c)(1),
(2), (4) Date: Apr. 1, 2004

(87) PCT Pub. No.: WO2004/014486

PCT Pub. Date: Feb. 19, 2004

(65) Prior Publication Data

US 2005/0019256 A1    Jan. 27, 2005

(30) Foreign Application Priority Data

Aug. 9, 2002 (CA) .................................. 2395584
Sep. 5, 2002 (RU) .............................. 2002123655
Mar. 13, 2003 (WO) .................... PCT/CA03/00351

(51) Int. Cl.
    *A61B 19/00* (2006.01)
(52) U.S. Cl. .............................. 128/898; 606/3; 607/88
(58) Field of Classification Search ................ 128/898; 606/3, 9, 15; 607/88, 89, 94
    See application file for complete search history.

(56) References Cited

U.S. PATENT DOCUMENTS 3,941,670 A    3/1976   Pratt, Jr.

(Continued)

FOREIGN PATENT DOCUMENTS

EP    0 619 100    10/1994

(Continued)

OTHER PUBLICATIONS

U.S. Appl. No. 10/119,976, Robert A. Ganz et al.

(Continued)

*Primary Examiner*—A. Farah
(74) *Attorney, Agent, or Firm*—John A. Merecki; Hoffman, Warnick & D'Alessandro LLC

(57) ABSTRACT

A method and an apparatus for the treatment of either endocavital infections or abnormal surface tissue conditions, particularly destructive bacterial infections, post major invasive surgery abscesses and skin infections such as vitiligo and psoriasis. If required, a catheter system is used, which allows the simultaneous drainage of an infected locus and irradiation of the infected locus with laser-generated pulsed ultraviolet light. The laser light wavelength is chosen so as to require radiation, which is lethal to the microorganisms causing the infection, at the lowest possible dose which will provide ameliorative therapy. Alternatively, a diode-pumped solid state Raman laser device is used which can be configured to provide in sequence a selected number of output wavelengths in the ultraviolet spectral range.

1 Claim, 1 Drawing Sheet

U.S. PATENT DOCUMENTS

| | | | |
|---|---|---|---|
| 3,948,772 A | 4/1976 | Ellner | |
| 3,971,947 A | 7/1976 | Lambert | |
| 4,017,735 A | 4/1977 | Siegel | |
| 4,115,280 A | 9/1978 | Pratt, Jr. | |
| 4,141,830 A | 2/1979 | Last | |
| 4,179,616 A | 12/1979 | Coviello et al. | |
| 4,255,383 A | 3/1981 | Schenck | |
| 4,265,747 A | 5/1981 | Copa | |
| 4,336,223 A | 6/1982 | Hillman | |
| 4,366,125 A | 12/1982 | Kodera | |
| 4,396,582 A | 8/1983 | Kodera | |
| 4,400,270 A | 8/1983 | Hillman | |
| 4,418,688 A | 12/1983 | Loeb | |
| 4,448,750 A | 5/1984 | Fuesting | |
| 4,464,336 A | 8/1984 | Hiramoto | |
| 4,471,225 A | 9/1984 | Hillman | |
| 4,482,809 A | 11/1984 | Maarschalkerweerd | |
| 4,615,799 A | 10/1986 | Mortensen | |
| 4,767,932 A | 8/1988 | Ellner | |
| 4,812,237 A | 3/1989 | Cawley et al. | |
| 4,871,559 A | 10/1989 | Dunn et al. | |
| 4,904,874 A | 2/1990 | Ellner | |
| 4,910,942 A | 3/1990 | Dunn et al. | |
| 4,983,307 A | 1/1991 | Nesathuria | |
| 4,983,411 A | 1/1991 | Tanaka et al. | |
| 5,004,541 A | 4/1991 | Noll et al. | |
| 5,034,235 A | 7/1991 | Dunn et al. | |
| 5,057,098 A * | 10/1991 | Zelman | 606/6 |
| 5,102,410 A | 4/1992 | Dressel | |
| 5,178,755 A | 1/1993 | LaCrosse | |
| 5,230,792 A | 7/1993 | Sauska et al. | |
| 5,236,595 A | 8/1993 | Wang et al. | |
| 5,242,439 A * | 9/1993 | Larsen et al. | 606/15 |
| 5,246,436 A | 9/1993 | Rowe | |
| 5,273,713 A | 12/1993 | Levy | |
| 5,320,617 A | 6/1994 | Leach | |
| 5,320,749 A | 6/1994 | Mullen | |
| 5,364,645 A | 11/1994 | Lagunas-Solar et al. | |
| 5,366,705 A | 11/1994 | Reidy | |
| 5,376,281 A | 12/1994 | Safta | |
| 5,403,308 A | 4/1995 | Wood et al. | |
| 5,415,655 A | 5/1995 | Fuller et al. | |
| 5,437,660 A | 8/1995 | Johnson et al. | |
| 5,593,404 A | 1/1997 | Costello et al. | |
| 5,741,244 A | 4/1998 | Klaas | |
| 5,800,165 A | 9/1998 | Torabinejad | |
| 5,900,211 A | 5/1999 | Dunn et al. | |
| 5,919,186 A * | 7/1999 | Bath | 606/6 |
| 5,957,404 A | 9/1999 | Doiron et al. | |
| 5,957,917 A | 9/1999 | Doiron et al. | |
| 6,094,767 A | 8/2000 | Iimura | |
| 6,152,919 A | 11/2000 | Hakky | |
| 6,200,309 B1 | 3/2001 | Rice | |
| 6,375,651 B2 * | 4/2002 | Grasso et al. | 606/15 |
| 6,464,625 B2 | 10/2002 | Ganz | |
| 6,491,618 B1 | 12/2002 | Ganz | |
| 6,764,501 B2 | 7/2004 | Ganz | |
| 6,962,583 B2 * | 11/2005 | Kadziauskas et al. | 606/6 |

FOREIGN PATENT DOCUMENTS

| | | |
|---|---|---|
| RU | 2141859 | 9/1998 |
| WO | WO 89 11260 | 11/1989 |
| WO | WO 93 19684 | 10/1993 |
| WO | WO 96 36396 | 11/1996 |
| WO | WO 99 01079 | 1/1999 |
| WO | WO 00/78393 A1 | 12/2000 |

OTHER PUBLICATIONS

Merck & Co., Inc., Online Article "Dorlands Medical Dictionary", Whitehouse Station, New Jersey, U.S.A., URL: www.merckmedicus.com/pp/us/hcp//thcp_dorlands.
"Interaction of Radiation With Matter", Online Article, URL: http://hyperphysics-phy-astr.gsu.edu/hbase/mod3.html.
"Interaction of Radiation With Matter", Online Article, URL: http://hyperphysics-phy-astr.gsu.edu/hbase/mod4.html.
"Terms and Definitions", Online Article, URL: www.dur.ac.uk/r.g.bower/Opticsl/revanswr/node8.html.
"Element 'Lines Extension'", Online Article, URL: www.spectraheap.com/manual/line-resolution.html.
Niosh, "The Registry of Toxic Effects of Chemical Substances", Online Article, URL: www.cdc.gov/niosh/rtecs/hz8583b0.html.
"Survival of Terrestrial Microorganisms on Spacecraft Components and Analog Mars Soil . . . ", Online Article URL: http://rtreport.ksc.nasa.gov/techreports/2001reports/600/609.html.
"Descriptions/definitions of Exposure Levels", Online Article URL: http://www.proscitech.com/au/catalogue/notes/exposure.htm.
LumeRx, "A New Approach To Managing Bacterial Infection", Online Article URL: http://www.lumerx.com.
B.U. Bridge, "Photonics Center Start-Up Targets Ulcer-Causing Bacteria", Online Article, URL: http://www.bu.edu/bridge/archive/2004/0402/photoincs.html.
Boston Business Journal, "LumeRx Medical Device Shines Light On Ulcer Cure", Article, Mar. 26-Apr. 1, 2004, vol. 24, No. 8.
Mendelson, Jack, MD, Research Paper, Montreal, Quebec, Canada, Apr. 22, 2004.
"Laser Device 'MARIA'", Brochure, Genestho Inc., Tallinn, Estonia.
"Principal Abbreviations 'The Rules'", Abbreviations Referenced in various Medical Reports (below).
"Great Medical Encyclopaedia 'Soviet Encyclopaedia'", Textbook, Publishing House, Moscow, Russia, 1977, vol. 7, pp. 439-440.
"Little Medical Encyclopaedia 'Soviet Encyclopaedia'", Textbook, Publishing House, Moscow, Russia, 1993, pp. 78-93.
B.N. Zgykov et al., 'Laser Technologies In Medicine', Report, Monograph, Samara, Russia, 2001.
V.G. Dobkin, "Medical Trials of the 'MARIA' Laser Therapeutic Device", Report, Moscow, Russia, 2002.
A.A. Vorob'ev, MD, PhD, "Protocol of Medical Tests For The Experimental Laser Device 'MARIA'", Report, Moscow, Russia, 2002.
A.A. Vorob'ev, MD, PhD, "Medical Trials of The 'MARIA' Laser Therapeutic Device", Report, Moscow, Russia, 2002.
V.P.Strel'tsov et al., "Protocol of Medical Tests For The Medical Laser Device 'MARIA'", Report, Moscow, Russia, 2002.
V.V. Yerokhin, PhD (M), "A Method For The Treatment of Destructive Pulmonary Tuberculosis By Endocavital Irradiation With Ultraviolet Laser Emissions", Report, Moscow, Russia.
V.V. Yerokhin, PhD (M), "Application of An Ultraviolet Radiation Spectrum, Generated By Laser Device 'MARIA', For The Endobronchial Treatment of Inflammatory Diseases of Bronchi of Specific (Tuberculosis) and Nonspecific Genesis", Report, Moscow, Russia, 2003.
F.K. Petrosian, "Protocol of Clinical Tests For The Medical Laser Device 'MARIA'", Report, Moscow, Russia, Apr. 16, 2004.
"The Small Medical Encyclopedia", 'Soviet Encyclopedia', Textbook, Moscow, Russia, 1991, pp. 136-138.
Ministry of Health Care of Russian Federation, Registration Certificate, Russia, Dec. 4, 2002.
Decision On The Issuance of The Patent For The Invention, Moscow, Russia, Feb. 16, 2005.
J Photochem Photobiol B. Jan. 1996;32(1-2): 59-65, "Ex-Vivo Treatment Of Gastric Helicobacter Infection By Photodynamic Therapy" by CE Millson et al., of the National Medical Laser Centre, University College London Medical School, UK, URL: http:www.ncbi.nlm.nih.gov/entrez/query.fcgi?CMD=Text&DB=pubmed, Retrieved On Oct. 19, 2004.
J Med Microbiol. Apr. 1996;44(4): 245-252, "The Killing Of Helicobacter Pylori BY Low-Power Laser Light In The Presence Of A Photosensitiser" by CE Millson et al., of the National Medical Laser Centre, University College London Medical School, UK, URL: http:www.ncbi.nlm.nih.gov/entrez/query.fcgi?CMD=Text&DB=pubmed, Retrieved On Oct. 19, 2004.

Drugs Exp Clin Res. 1986;12(4) :335-342, "Bacterial Effects Induced By Laser Irradiation And Haematoporphyrin Against Gram-Positive And Gram-Negative Microorganisms" by P. Martinetto et al. URL: http:www.ncbi.nlm.nih.gov/entrez/query.fcgi?CMD=Text&DB=pubmed, Retrieved On Oct. 19, 2004.

Blood Purif. 1991;9(2) :102-108, "In Vitro Studies On The Microbicidal Effectiveness Of A Xenon-Based Ultraviolet Light Device For Continuous Ambulatory Peritoneal Dialysis Connections" by W. Kubey et al. of the Renal Division, Baxter Healthcare Corp., Round Lake, I11, URL: http:www.ncbi.nlm.nih.gov/entrez/query.fcgi?CMD=Text&DB=pubmed, Retrieved On Oct. 19, 2004.

"Ultraviolet Radiation", Alternative Disinfectants And Oxidants, EPA Guidance Manual, Chapter 8, Apr. 1999.

Danilin, Prof. Nikolai A., M.D., Ph.D. "Vitiligo", Educational Brochure, Academy of Laser Sciences, Moscow, Russia, Sep. 2003.

Vitta AG, Newest Medical Laser Technologies, Corporate Brochure, Russia 2002.

Plettenberg, H. et al., "Childhood Vitiligo and Tacrolimus, Immunomodulating Treatment for an Autoimmune Disease", Arch Dermatol. 2003; 139:651-654, USA.

Asawanonda, P. et al., "308-nm Excimer Laser for the Treatment of Psoriasis: A dose-Response Study", Arch Dermatol. 2000; 136:619-624, USA.

Blood Purif. 1991;9(2) :102-108, In Vitro Studies On The Microbicidal Effectiveness Of A Xenon-Based Ultraviolet Light Round Lake, I11, URL: http:www.ncbi.nlm.nih.gov/entrez/query.fcgi?CMD=Text&DB=pubmed, Retrieved On Oct. 19, 2004.

* cited by examiner

METHOD FOR TREATMENT OF INFECTIONS WITH ULTRAVIOLET LASER LIGHT

BACKGROUND OF THE INVENTION

1. Field of the Invention

This invention relates to a method and apparatus for the treatment of infections, particularly abscesses such as cavernous tuberculosis, post-surgical intra-abdominal tissue conditions such as ulcers, vitiligo and psoriasis. More specifically, this invention relates to a system which allows the simultaneous drainage of an infected space and irradiation of an infected locus with laser-generated ultraviolet light. Additionally, this invention relates to a system which allows the simultaneous drainage of an endo-cavital space and irradiation of an infected locus with laser generated ultraviolet light.

2. Related Art

The use of ultraviolet light is a known and proven technique in procedures for sterilising liquids and for rendering drinking water safe for public consumption. For these purposes, short wavelength, spectrally non-selective ultraviolet light is used having a wavelength of from about 200 nm to about 350 nm. Within the so-called UV-C wave length range (200-270 nm), ultraviolet light is most effective in destroying the microorganisms commonly found in untreated water. Typical procedures are described by Dunn et al. in U.S. Pat. No. 5,900,211; by Nesathurai in U.S. Pat. No. 4,983,307; and by Wang et al. in U.S. Pat. No. 5,236,595.

It is generally accepted that microorganisms can be broadly grouped into five basic families; these are bacteria, viruses, fungi, protozoa and algae. These five families have different properties, occur in different habitats and respond differently to microbiocides such as antibiotics. Bacteria, fungi, protozoa and algae are generally characterised as comprising a cell wall, a cytoplasmic membrane and genetic material which is essentially DNA material. Viruses are somewhat different and generally have an outer coating of proteins surrounding genetic material which again is DNA material. When harsh ultraviolet light penetrates the microorganism, it causes disruption of chemical bonds within the DNA system thus preventing the DNA replication step required for reproduction of the microorganism. If a microorganism cannot reproduce itself, it is effectively dead.

However, the cells of different microorganisms are not the same: different microorganisms have different sensitivities to different wavelengths of light within the UV range; also the dose of UV light required to effect microorganism destruction varies for different microorganisms. The dose (or accumulated energy) is a product of the time for which the microorganism is exposed to the radiation, and the radiation power; most commonly, power is measured in Watts (W), and time is measured in seconds. This approach also appears to be applicable to vitiligo and psoriasis infections, even though microorganisms are not involved. Indeed for both of these infections the etiology is poorly understood and the causative agents for these infections have not been identified.

TABLE 1

Average lethal dose densities for different microorganisms (in mWsec/cm$^2$) measured under a non-selective UV irradiation (a Xenon lamp with a UV band filter centered at 254 nm).

| Microorganism | Dose/cm$^2$ | Microorganism | Dose/cm$^2$ |
|---|---|---|---|
| Bacillus anthracis | 8.8 | Dysentery bacilli | 4.2 |
| Shigella dysentariae | 4.3 | Escherichia coli | 7.0 |
| Shigella flexneri | 3.4 | Streptococcus faecalis | 10.0 |
| Corynbacterium diphtheriae | 6.5 | Staphylococcus epidermis | 5.8 |
| Vibri commo (cholera) | 6.5 | Bacteriophage (E. coli) | 6.5 |
| Hepatitis | 8.0 | Salmonella | 10.0 |
| Influenza | 6.6 | Baker's yeast | 8.8 |
| Legionella pneumophilia | 3.8 | Mycobacterium tuberculosis | 10.0 |
| Salmonella paratyphi | 6.1 | Polio virus | 7.0 |
| Salmonella typhosa | 7.0 | | |

Table 1 shows that for different microorganisms, the measured lethal dose (in vitro) is not constant.

In addition to using UV light to sterilise fluids such as drinking water, lasers generating spectrally narrow-line light in ranges other than in the UV range have also had some use in medical therapy. In this context, it is relevant to distinguish between the use of non-UV lasers for surgical and other techniques and the use of UV light to treat microorganism infections. For example, in some therapeutic procedures, He—Ne or Nd-YAG lasers are used as localised heat sources, which stimulate blood supply and heat or destroy selected tissues; these laser radiation wavelengths are generally in the red or near infrared ranges. Any microorganisms present will only be affected by the laser irradiation if the heat generated by the laser causes the temperature of the microorganism to reach or exceed about 40° C. Although temperatures in this range are lethal to many microorganisms, the use of such lasers as a therapeutic tool to control microorganisms is circumscribed by the unacceptable damage this level of temperature can cause to surrounding uninfected tissues.

The treatment of destructive forms of endo-cavital infections, such as tuberculosis and post-surgical intra-abdominal abscesses, is a particularly difficult therapeutic area. The pathologically changed structures of cavital walls and substantial amounts of pus inside cavities prevent efficient administration of antibiotics. Also, many pathogens causing endo-cavital infections have become antibiotic-resistant. Similar considerations apply to the treatment of abnormal surface tissue lesions, such as abcesses, ulcers, vitiligo and psoriasis.

The procedures used at present to deal with endo-cavital infections are not as effective as is desired; a two step therapy is generally used. First, the cavity is drained to remove as much material as possible; this will include both cell debris due to the infection and to some extent the microorganisms causing the infection. Second, an antibiotic medication is administered to the patient. If the antibiotic(s) are to be successful, maximal cavity drainage is essential. In order to achieve maximal drainage, a hollow catheter is inserted cutaneously into the cavity either blindly or with guidance. Guidance is normally effected either by the use of an ultrasonic probe, or by the use of an endoscopic fiber-optic device included in the drainage catheter. But drainage is hampered by the flow characteristics of the fluid and pus containing cell debris being removed from the cavity, and by the relatively small size of the catheter in comparison with the potential volume of the cavity requiring drainage. An additional problem is the unavoidable presence of microorganisms both elsewhere in the cavity and on and around the catheter. As a consequence of these difficulties, in practice it is rarely possible to drain a cavity to the desirable level. It is also of importance that there is a real risk that some of the microorganisms are the so-called "super bugs", which are mutant strains of common microorganisms such as staphylococcus; these strains are resistant to the currently available antibiotics.

Endo-cavital infection-caused diseases, such as destructive forms of tuberculosis and post-surgical intra-abdominal abscesses, present a rapidly growing concern internationally. In North America, post-surgical intra-abdominal abscesses are a major post-operative problem for a wide range of invasive surgical procedures. It has been estimated that the percentage of patients who develop post-surgical intra-abdominal abscesses ranges from about 30% for colorectal surgery, through about 15% for pancreatic or biliary surgery to about 2% for gynecologic surgery. Patients undergoing intra-abdominal surgery in North America alone, on an annual basis, number in the millions. These infections can be traced to several causes, including both airborne microorganisms and spontaneous leaks or perforations of either the biliary tract or the intestines. In other words, any procedure devised to treat such infections has to accommodate the fact that the infection will almost certainly involve several strains of microorganisms; each strain will respond differently to any applied procedure. Again, many of these considerations apply to abnormal surface tissue conditions.

It has been reported by Apollonov et al. in RU 2141859 (issued in 1998) that laser-generated ultraviolet light can be used in treating tuberculosis. By using a suitable fiber-optic catheter, the laser-generated UV light is used to irradiate and to destroy, within the lung cavern, the microorganisms, which are the cause of the tubercular infection. The method includes puncturing or draining the destructive cavern in the lungs, evacuating the purulent contents of the cavern and then exposing the interior surface of the cavern to ultraviolet laser radiation. This involves 10 to 12 minutes of exposure to the defocussed pulsed radiation of a solid-state laser at a wavelength from about 220 nm to about 290 nm, and energy density of 200 mWsec/cm$^2$ with the pulse repetition frequency controlled as a function of the degree of destruction in the lungs, to ensure irradiation with an average energy density of 10 to 15 mWsec/cm$^2$. A treatment session is concluded with a single introduction of 1.0 units of streptomycin or canamycin into the cavern. A course of treatment comprises 10-12 sessions of laser irradiation of the cavern.

However, there are several difficulties with the apparatus and the procedure described by Apollonov et al. These are as follows.
(1) The need for repeated puncturing of the cavern, which increases the degree of trauma experienced by the patient.
(2) Before the procedure is carried out, each repeated puncturing requires repeated radiological investigations, which increase the X-ray dose to which the patient is subjected.
(3) Each treatment session is concluded with a single introduction into the cavern of a full daily dose of an anti-tubercular medication dissolved in 2 to 3 ml of a 0.5% Sol. Novocain. The introduction of a full daily dose of anti-tubercular medication in a single dosage unit does not permit maintaining its bactericidal concentration within the cavern at a steady level throughout a period of 24 hours. In addition, because of the quantity involved, an introduction of such an amount of anti-tubercular medication at once frequently causes irritation of the mucous tissue of the bronchi draining the cavern, and this leads to a debilitating cough and expectoration in the sputum of a considerable quantity of the anti-tubercular medication that was introduced into the cavern; it also reduces the concentration of medication and lowers its bactericidal effect.
(4) To irradiate the cavern, Appolonov et al. used the emission of an available laser generating within the UV-C spectral range (266 nm, the fourth harmonic of the Nd:YAG laser). While that wavelength is still capable of producing bactericidal effect on tuberculosis pathogens, it is apparently not optimal for destroying the majority of tuberculosis microorganisms. This relationship is shown graphically in FIG. 1. Inspection of FIG. 1 shows that the most efficient wavelength to kill tuberculosis bacteria is about 250 nm, and that some UV wavelengths may not be efficient at all to treat tuberculosis. At the same time, other bacteria are more susceptible to the wavelengths efficient in the tuberculosis treatments. The use of a UV light wavelength which is not the most efficient wavelength, while it has specific values characteristic of each microorganism strain, or class of strains, means increased exposures, higher irradiation energy density and an increased risk of side effects.

Usually, patients to receive antibacterial treatment are already under a major stress, often with depressed immune systems after having undergone a major invasive surgical procedure, or suffering from a severe infection such as tuberculosis or intra-abdominal abscess. Thus, it is very desirable that any treatment procedure to deal with such infections would expose the patient to as little further stress as possible. It is therefore a prime concern to avoid having to surgically re-enter the cavity. The traumatic levels associated with repeated cavity re-entry implies that the level of antibiotics required to control the so-called "super bugs" may be more than the weakened patient can tolerate. Yet again, similar considerations often apply to abnormal surface tissue conditions such as ulcers and abscesses.

SUMMARY OF THE INVENTION

This invention results from establishing the fact that the lethal dose required for a given microorganism depends on the wavelength of the irradiating ultraviolet light. By matching the wavelength of the UV light to a specific microorganism, or class of microorganisms, the lethal dose is optimized, the irradiation efficiency is increased and the risk of damaging surrounding tissues is minimized as the amount of UV radiation to which the patient is exposed can be minimised.

It was shown in the Table 1 above that the lethal doses of the UV light are not the same for different strains of microorganisms. Although no microorganimsms appear to be involved, the same logic appears to apply to vitiligo and psoriasis. The UV-irradiation used in the measurements summarized in Table 1 was spectrally non-selective. The results of treating (in vitro) different microorganisms with narrow band laser generated UV light, spectrally matching the most efficient bactericidal response (found by measuring curves for various bacteria similar to that of FIG. 1), are shown in Tables 2 and 3. The average lethal doses for different bacterial strains irradiated with narrow band laser light are substantially lower as compared to those shown in Table 1.

TABLE 2

Measured average lethal doses for different microorganisms (in mWsec) measured under specific laser-line irradiation

| Cavern Area (cm$^2$) | LETHAL DOSE (mWsec) | | | | | |
|---|---|---|---|---|---|---|
| | Micro-bacterium tuberculosis | St. Aureus | Klebsiella pneumonia | Enterobacter aerogenes | Pseudomonas aeruginos | E. coli |
| 28.3 | 45 | 85 | 141 | 198 | 141 | 141 |
| 50.3 | 80 | 151 | 251 | 352 | 251 | 251 |
| 78.5 | 126 | 236 | 393 | 550 | 393 | 393 |
| 113.1 | 181 | 339 | 565 | 792 | 565 | 565 |
| 153.9 | 246 | 462 | 770 | 1078 | 770 | 770 |
| 201.1 | 322 | 603 | 1005 | 1407 | 1005 | 1005 |
| 254.5 | 407 | 763 | 1272 | 1781 | 1272 | 1272 |
| 314.2 | 503 | 942 | 1571 | 2199 | 1571 | 1571 |
| 380.1 | 608 | 1140 | 1901 | 2661 | 1901 | 1901 |
| 452.4 | 724 | 1357 | 2262 | 3167 | 2262 | 2262 |
| 530.9 | 849 | 1593 | 2655 | 3717 | 2655 | 2655 |
| 615.8 | 985 | 1847 | 3079 | 4310 | 3079 | 3079 |
| 706.9 | 1131 | 2121 | 3534 | 4948 | 3534 | 3534 |

TABLE 3

Average lethal dose densities (dose/cm$^2$) for different microorganisms measured under laser-line irradiation specific to each bacteria (based on the Table 2 data).

| | AVERAGE LETHAL DOSE DENSITY (mWsec/cm$^2$) Micro-organism | | | | | |
|---|---|---|---|---|---|---|
| | Micro-bacterium tuberculosis | St. Aureus | Klebsiella pneumonia | Enterobacter aerogenes | Pseudomonas aeruginos | E. coli |
| Dose/cm$^2$ | 1.6 | 3 | 5 | 7 | 5 | 5 |

Thus in a first broad embodiment this invention seeks to provide a method for treating either endo-cavital infections or abnormal surface tissue conditions comprising:
 (a) selecting an ultraviolet light wavelength at which the effective dose in microwatt seconds/cm$^2$ is minimised;
 (b) if required, draining the infected locus to remove any debris contained therein;
 (c) irradiating the infected locus with pulsed laser-generated ultraviolet light having a wavelength close to the wavelength selected in step (a); and
 (d) if required, repeating steps (b) and (c) until a desired level of ameliorative therapy has been achieved.

In a second broad embodiment this invention seeks to provide a method for treating either endo-cavital infections or abnormal surface tissue conditions comprising:
 (a) determining the spectrum of microorganisms present in the population of microorganisms in the cavity or in the tissue causing the infection;
 (b) determining a ranking of the relative amounts of at least the major infecting microorganisms within the population present;
 (c) selecting an ultraviolet light wavelength at which the lethal dose in microwatt seconds/cm$^2$ is minimised for at least the highest ranking organism identified in step (b);
 (d) if required, draining the infected locus to remove any debris contained therein;
 (e) irradiating the infected locus with pulsed laser-generated ultraviolet light having a wavelength close to the wavelength selected in step (c); and
 (f) if required, repeating steps (d) and (e) until a desired level of ameliorative therapy has been achieved.

In a third broad embodiment this invention seeks to provide an apparatus for treating an infected locus, selected from the group consisting of an endo-cavital infection and an abnormal surface tissue condition, comprising in combination:
 (A) a catheter device constructed and arranged to be both applied to and removed from the infected locus;
 (B) a laser generating device constructed and arranged to provide at least one output of pulsed ultraviolet light of known intensity and wavelength of from about 200 nm to about 700 nm; and
 (C) a drainage system constructed and arranged to remove fluid debris from the infected locus;

wherein:
 (i) the catheter device includes at least one fibre optic guide constructed and arranged to deliver ultraviolet light generated by the laser device to a locus within the cavity; and
 (ii) the laser generating device is chosen from the group consisting of a laser generating device constructed and arranged to provide a beam of ultraviolet light of a single predetermined wavelength and intensity, and a laser device constructed and arranged to provide a plurality of beams of ultraviolet light each having a known wavelength and intensity.

Preferably the at least one fibre optic device is constructed and arranged to provide a beam of ultraviolet light is a single use device.

Preferably, the laser generating device is a tunable Raman solid state laser. Conveniently, the laser generating device is a diode pumped tunable Raman solid state laser.

Preferably, the catheter device includes at least a fibre optic guide connectable to the laser and constructed and arranged to permit illumination of the cavity, and a separate pumpable drainage system Preferably, the catheter device additionally includes a second fibre optic system constructed to permit viewing of the interior of the cavity.

Alternatively, the catheter device also includes an ultrasonic probe system.

Preferably, the catheter device also includes a drainage system constructed and arranged to remove fluid debris from the infected locus.

DETAILED DESCRIPTION OF THE INVENTION

Figure 1:
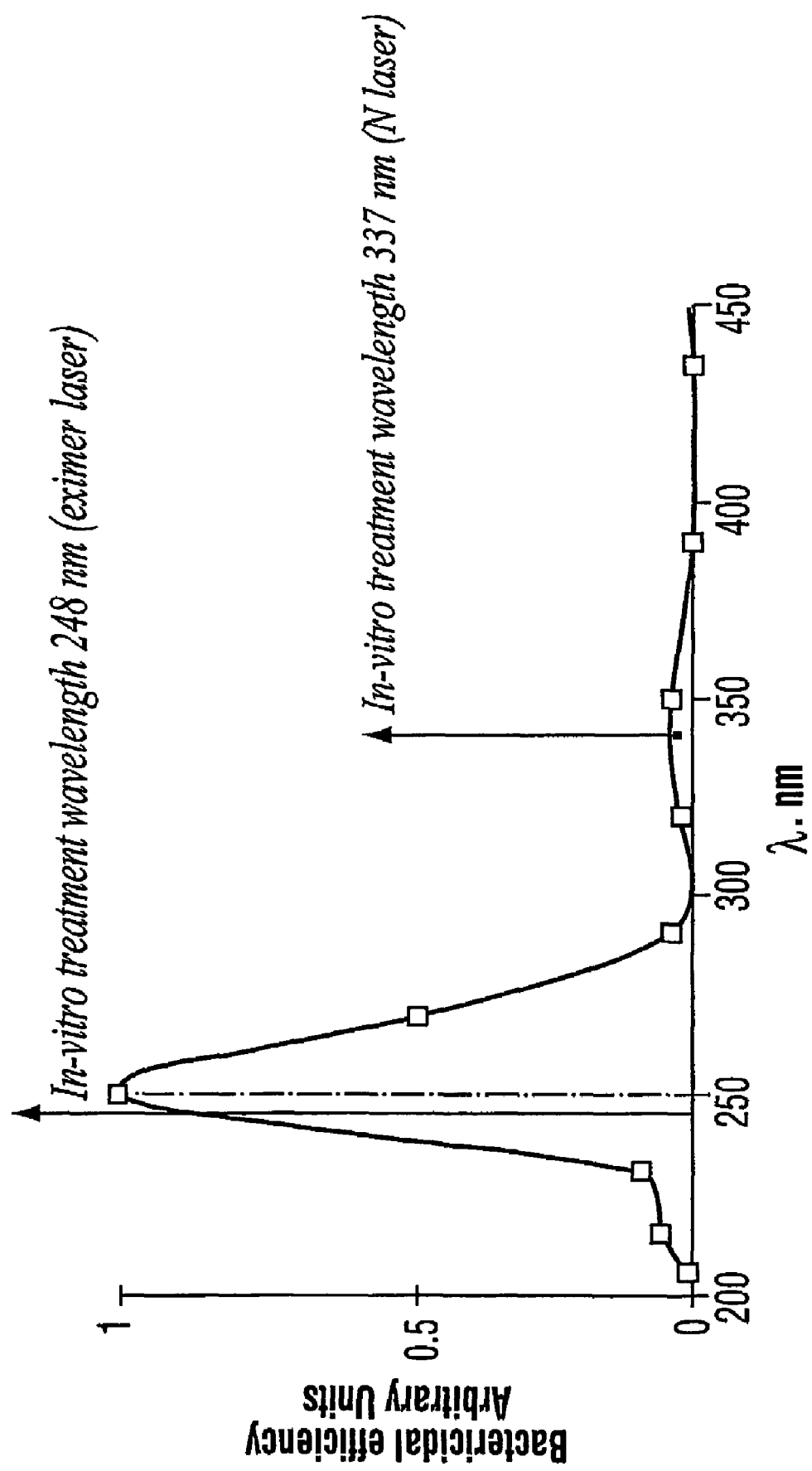
FIG. 1 depicts a relationship between bactericidal efficiency and wavelength in accordance with the related art.

This invention derives from the discovery that, although it is known that broad spectrum ultraviolet light is lethal to a wide variety of known microorganisms, including viruses which are extremely resistant to antibiotics, hitherto it had not been fully understood that there is a "best" frequency for each microorganism at which ultraviolet light is most lethal to that microorganism. This logic also appears to apply to both vitiligo and psoriasis even though the causative agent for both of these has yet to be identified. This approach permits the use of the lowest dose, in microwatts/cm$^2$, to achieve the desired level of ameliorative therapy. But this also raises a difficulty, which is that laser generating devices provide a laser beam with only a very narrow wavelength range: a laser provides an essentially monochromatic beam. It then follows that if a laser device is used, although such a device may be tunable to some extent to provide a wavelength either at, or at least close to, the desired most lethal wavelength, it will only provide one wavelength which will be most lethal for only one microorganism (or a group of closely similar microorganisms). But as noted above, in the typical case of major invasive abdominal surgery the infections are caused by more than one microorganism, typically a spectrum of microorganisms is present in the cavity and the population as a whole is causing the infection. To deal with such a broad spectrum of microorganisms a plurality of laser devices will be required.

An alternative laser source has recently become available which overcomes these difficulties. This is the so-called diode pumped-solid state Raman laser. These are compact solid state devices which operate at a high repetition rate and can be configured to provide more than one output frequency by interposing in sequence different Raman materials into the pulsed laser beam. These devices also operate reliably at high pulse repetition rates of the order of 0.2 kHz. It is thus now possible to obtain what is effectively a tunable laser device which can be tuned to be most lethal to more than one of the microorganisms causing an infection in a bodily cavity either after major invasive surgery, or due to other causes, for example an inner ear infection. Laser devices of this type are available from Passat Ltd, Toronto, Ontario, Canada. A typical device can provide up to nine different wavelengths adjusted to the needed wavelength within the range of from about 200 nm to about 1200 nm. These devices are small, compact, require no dangerous gases, and are well adapted for use in a medical facility.

The method provided by this invention requires as a first step an assessment of the infected locus to determine the ultraviolet wavelength at which the required effective dose is minimised. Since most infections involve the presence of microorganisms, this first step will usually require an assessment of the microorganisms to identify both the members of the population and to rank them as a proportion of the population. It is then possible to assess the most lethal wavelength for each of the microorganisms, for example by means of tests carried out on microorganism samples from one of the available collections. For infections such as vitiligo and psoriasis a similar assessment is also possible. A data bank can then be developed which will cross reference each microorganism or infection to the most desirable irradiation frequency. As but one example, it has been determined the most lethal wavelengths for tuberculosis, vitiligo and psoriasis are each at about 248 nm and about 337 nm, with the longer wavelength being far less effective. At the same time as establishing the most lethal wavelength it is also desirable to establish the most effective laser pulse frequency.

The next step then is to provide a laser generating device which will provide either the most desirable wavelength for the highest ranking microorganism in the population, or for the three or four highest ranking ones. The infected locus is then irradiated to provide a desired radiation dose in microwatts/cm$^2$ to the infected locality within the space. The patient is then monitored over a suitable time period to assess whether the cavity needs to be irradiated a second time.

The irradiation at a selected wavelength or wavelengths can also be accompanied by conventional antibiotic therapy.

It is also contemplated within the scope of this invention that in order to minimise patient stress a single multichannel catheter is used which will contain at least both the fibre optics required for the laser and the channels required for effective drainage and lavage. For the adequate treatment of at least infections, especially endo-cavity infections, it is desirable for the medical personnel to be able to view the inside of the cavity either directly using visible light fibre optic devices or indirectly using an ultrasonic probe. Catheter devices of this type are known; typical catheters of these types including a laser capability, drainage channels, and the like are described by among others by Johnson et al. in U.S. Pat. No. 5,437,660; Costello et al. in U.S. Pat. No. 5,593,404 and Doiron et al. in U.S. Pat. No. 5,957,404.

We claim:

1. A method of treating an infected locus having a population comprising at least one type of microorganism, the method comprising:
 (a) identifying member types present in the population;
 (b) ranking the member types and determining a targeting sequence commencing with a first member based on respective proportions of the member types in the population;
 (c) selecting an ultraviolet light wavelength in a spectral range corresponding to at least the first member in the targeting sequence to provide a predetermined bactericidal radiation dose to the infected locus;
 (d) selectively draining the infected locus to remove any biological debris contained therein;
 (e) irradiating the infected locus with laser generated ultraviolet light having a wavelength substantially equal to the wavelength selected in step (c); and
 (f) repeating steps (c) to (f) for subsequent members in the targeting sequence.

* * * * *

UNITED STATES PATENT AND TRADEMARK OFFICE
CERTIFICATE OF CORRECTION

PATENT NO. : 7,409,954 B2   Page 1 of 1
APPLICATION NO. : 10/491426
DATED : August 12, 2008
INVENTOR(S) : Dobkine et al.

It is certified that error appears in the above-identified patent and that said Letters Patent is hereby corrected as shown below:

Title Page, Item (57) ABSTRACT, line 4 after the word "skin", delete "infections", and insert -- conditions --, and line 11, correct the spelling of "therapty" to -- therapy --.

Column 1, Field of the Invention, line 10, after "tuberculosis", delete "post-surgical intra-abdominal", and line 11, after the word "as", insert -- intra-abdominal and superficial infections --. Line 56, after the word "for", delete "these infections", and insert -- the latter conditions --.

Column 8, line 14, after the word "desirable", delete "irradiation", and insert -- optical --, and after "frequency", insert -- of irradiation --. Line 20, after "effective", delete "laser pulse frequency", and insert -- laser irradiation dose --.

Signed and Sealed this
Twenty-ninth Day of May, 2012

David J. Kappos
*Director of the United States Patent and Trademark Office*